US009045790B2

(12) United States Patent
Tsukada (10) Patent No.: US 9,045,790 B2
(45) Date of Patent: Jun. 2, 2015

(54) ANALYSIS DEVICE

(75) Inventor: Masashi Tsukada, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 55 days.

(21) Appl. No.: 13/455,555

(22) Filed: Apr. 25, 2012

(65) Prior Publication Data

US 2012/0273368 A1 Nov. 1, 2012

(30) Foreign Application Priority Data

Apr. 26, 2011 (JP) ................................ 2011-098742
Apr. 5, 2012 (JP) ................................ 2012-086736

(51) Int. Cl.
*G01N 27/30* (2006.01)
*G01N 27/26* (2006.01)
*G01N 27/327* (2006.01)
*C12Q 1/00* (2006.01)

(52) U.S. Cl.
CPC ................ *C12Q 1/004* (2013.01); *C12Q 1/006* (2013.01); *G01N 2333/902* (2013.01); *G01N 2333/904* (2013.01)

(58) Field of Classification Search
CPC .. C12Q 1/004; C12Q 1/006; G01N 2333/904; G01N 2333/902
USPC ................. 205/775; 204/400, 403.01–403.14
See application file for complete search history.

(56) References Cited

U.S. PATENT DOCUMENTS

| 4,840,893 | A | * | 6/1989 | Hill et al. ...................... 435/6.16 |
| 5,262,035 | A | * | 11/1993 | Gregg et al. ............. 204/403.11 |
| 5,972,199 | A | | 10/1999 | Heller et al. |
| 6,060,327 | A | | 5/2000 | Keen |
| 6,676,816 | B2 | | 1/2004 | Mao et al. |
| 6,932,894 | B2 | | 8/2005 | Mao et al. |
| 7,611,621 | B2 | * | 11/2009 | Cai et al. .................... 205/777.5 |
| 7,807,835 | B2 | | 10/2010 | Xie et al. |

FOREIGN PATENT DOCUMENTS

| DE | 4442253 A1 | 5/1996 |
| JP | 01-235593 A | 9/1989 |
| JP | 08-015431 B | 2/1996 |
| JP | 2002-514305 A | 5/2005 |
| JP | 2005-520172 A | 7/2005 |
| JP | 2006-509837 A | 3/2006 |
| JP | 2006-234788 A | 9/2006 |

(Continued)

OTHER PUBLICATIONS

Sung et al. (Biosens. Bioelect. 18, 2003, 1231-1239).*

(Continued)

*Primary Examiner* — Luan Van
*Assistant Examiner* — Steven Rosenwald
(74) *Attorney, Agent, or Firm* — Morgan, Lewis & Bockius LLP (57) ABSTRACT

An analysis device is disclosed which includes an electron detection medium to obtain information needed for analyzing an analyte in correlation with an electron transfer level, and a reagent part which is disposed on the electron detection medium and includes an electron transporting substance to transport electrons between the analyte and the electron detection medium, the electron transporting substance including a water-soluble aromatic heterocycle compound, and being free of a metal complex. An analysis method using the analysis device is also disclosed.

15 Claims, 7 Drawing Sheets

(56) References Cited

FOREIGN PATENT DOCUMENTS

| WO | 88/08447 A1 | 11/1988 |
|----|-------------|---------|
| WO | 93/23748 A1 | 11/1993 |
| WO | 98/52042 A1 | 11/1998 |
| WO | 03/085372 A2 | 10/2003 |

OTHER PUBLICATIONS

Palmisano et al. (Biosens. Bioelect. 15, 2000, 531-539).*
"Sigma_Meldola", http://www.sigmaaldrich.com/catalog/product/sigma/d8142?lang=en&region=US, accessed May 20, 2014.*
Delocalization of Electrons, accessed at http://chemwiki.ucdavis.edu/Theoretical_Chemistry/Chemical_Bonding/Valence_Bond_Theory/Resonance/Delocalization_of_Electrons on Oct. 16, 2014.*
Koopal et al. "Glucose sensor utilizing polypyrrole incorporated in track-etch membranes as the mediator," Biosensors & Bioelectronics, 7:461-471 (1992).
Kros et al. "Poly(3,4-ethylenedioxythiophene)-Based Glucose Biosensors," Advanced Materials, 13: 1555-1557 (2001).
Kros et al. "Poly(pyrrole) versus poly(3,4-ethylenedioxythiophene): implications for biosensor applications," Sensors and Actuators B, 106: 289-295 (2005).
Extended Search Report issued in corresponding European Patent Application No. 12165202.8 dated Oct. 1, 2012.

* cited by examiner

ANALYSIS DEVICE

CROSS-REFERENCE TO RELATED APPLICATION

This application claims priority under 35 USC 119 from Japanese Patent Application No. 2011-098742 filed on Apr. 26, 2011, and Japanese Patent Application No. 2012-086736 filed on Apr. 5, 2012, the disclosures of which are incorporated by reference herein.

BACKGROUND

1. Technical Field

The present invention relates to an analysis device.

2. Related Art

As methods for measuring various substances contained in biological samples such as blood, for example, methods with enzyme sensors using enzymes are known. In an enzyme sensor utilizing an electrochemical reaction system in which a general enzyme is used, a signal is obtained by detecting, on an electrode surface, a transfer of electrons generated based on an enzymatic catalytic reaction. Even when a colorimetric reaction system, which depends on changes in the optical properties of a pigment, is used as a detection method, its basic reaction is derived from the enzymatic catalytic reaction (oxidation-reduction) and involves electron transfer. In these reaction systems, electron transport efficiency in the reaction systems influences detection sensitivities. Various techniques in which the electron transport efficiency is improved in order to increase the sensitivity of enzyme sensors are known.

For example, National phase publication (Translation of PCT Application) No. 2002-514305 discloses a sensor in which a surface of an electrode is modified with a substance having a helical structure, such as nucleic acid, as a conductive polymer, to promote electron transfer to or from an enzyme molecule to be targeted.

Since electron transfer between an electrode and an enzyme occurs through the active center of the enzyme, the manner of the arrangement of a site, in which the active center is present, with respect to the electrode is important. In order to decrease influences on the orientation of the active center of an enzyme and therefore to transport electrons efficiently, molecules which function like an electron transport mediator which is oxidized/reduced to transport electrons, for example, complexes having, as an active center, a transition metal such as iron, copper, osmium, or ruthenium, are known, and sensors using such a complex are also known (for example, see Japanese National phase publication (Translation of PCT Application) Nos. 2006-509837 and 2005-520172).

As an enzyme electrode, a system in which a polypyrrole is used is known (for example, Biosensors & Bioelectronics, Vol. 7, (1992) pp. 461-471 and Sensors and Actuators B, Vol. 106, (2005) pp. 289-295). Since pyrrole, which is a monomer, has poor water-solubility, it is not possible to directly mix pyrrole with an enzyme liquid to prepare an enzyme electrode on the surface of an electrode material. Therefore, for example, in these documents (i.e., Biosensors & Bioelectronics, Vol. 7, (1992) pp. 461-471 and Sensors and Actuators B, Vol. 106, (2005) pp. 289-295), a polymerization reaction is carried out using ferric chloride and a pyrrole solution in a track etched membrane and, thereafter, the membrane is impregnated with an enzyme liquid to obtain an electrode.

SUMMARY OF THE INVENTION

However, there is still room for improvement with respect to the sensitivity of analysis devices such as sensors for detecting analytes in samples. In a sensor, a higher detection sensitivity not only allows detection of a small amount of analyte in a sample, but also becomes advantageous when miniaturization of the sensor in itself is required. In addition, a metal complex used as an electron transport mediator is generally an expensive material and may become unstable as a substance or interfere with a reaction potential since the metal complex in itself is oxidized and reduced.

Further, with respect to an enzyme electrode in which a polypyrrole is used, a manufacturing method thereof is complicated. Moreover, when voltage is continuously applied to polypyrrole in an aqueous system environment, polypyrrole may be decomposed (see Sensors and Actuators B, Vol. 106, (2005) pp. 289-295), and, therefore, the long-time use reliability may be low when using an enzyme electrode in which polypyrrole is used.

Thus, an analysis device that has higher sensitivity and reliability than those conventionally used in the art by using an electron transporting substance with stability has been demanded.

Accordingly, it is an object of the present invention to provide an analysis device that has higher sensitivity and reliability than those conventionally used in the art; and also to provide an analysis method using the analysis device.

Exemplary embodiments of the present invention include the followings, but the present invention is not limited to the following exemplary embodiments.

<1> An Analysis Device Comprising:

an electron detection medium to obtain information needed for analyzing an analyte in correlation with an electron transfer level; and a reagent part which is disposed on the electron detection medium and comprises an electron transporting substance to transport electrons between the analyte and the electron detection medium, the electron transporting substance comprising a water-soluble aromatic heterocycle compound, and being free of a metal complex.

<2> The analysis device according to <1>, wherein the electron transporting substance comprises at least one water-soluble aromatic heterocycle compound selected from the group consisting of pyridine compounds and imidazole compounds (the group consisting of pyridine, imidazole and derivatives thereof).

<3> The analysis device according to <1> or <2>, wherein the water-soluble aromatic heterocycle compound has a molecular weight of 1,000 or less.

<4> The analysis device according to any one of <1> to <3>, wherein the reagent part further comprises an electron transfer compound that transfers an electron to or from the analyte.

<5> The analysis device according to <4>, wherein the electron transfer compound is an oxidoreductase.

<6> The analysis device according to <4> or <5>, wherein a concentration of the electron transporting substance is a concentration that allows transportation of electrons between the electron detection medium and the electron transfer compound.

<7> The analysis device according to any one of <1> to <6>, wherein a concentration of the electron transporting substance is from 10 mass % to 60 mass % based on a total mass of the reagent part.

<8> The analysis device according to any one of <1> to <7>, wherein the electron transporting substance comprises at least one water-soluble aromatic heterocycle compound selected from the group consisting of pyridine and aminomethyl pyridine.

<9> The analysis device according to any one of <1> to <8>, wherein the reagent part comprises a crosslinked substance.

<10> The analysis device according to any one of <1> to <9>, wherein the reagent part comprises a crosslinked substance obtained by crosslinking using at least one selected from the group consisting of glutaraldehyde, carbodiimide compounds and succinimide esters.

<11> The analysis device according to any one of <1> to <10>, wherein the electron detection medium is an electric conductor.

<12> The analysis device according to any one of <1> to <11>, wherein the analyte is a saccharide.

<13> An analysis method comprising obtaining information needed for analyzing an analyte based on an electron transfer level of the analyte using the analysis device according to any one of <1> to <12>.

BRIEF DESCRIPTION OF THE DRAWINGS

Exemplary embodiments of the present invention are described in detail based on the following figures, wherein.

DETAILED DESCRIPTION OF THE INVENTION

An analysis device according to the present invention includes: an electron detection medium to obtain information needed for analyzing an analyte in correlation with an electron transfer level; and a reagent part which is disposed on the electron detection medium and includes an electron transporting substance to transport electrons between the analyte and the electron detection medium, the electron transporting substance including a water-soluble aromatic heterocycle compound, and being free of a metal complex.

An analysis method according to the present invention includes obtaining information needed for analyzing an analyte based on an electron transfer level of the analyte using the analysis device.

According to the present invention, electrons are efficiently transported between the analyte and the electron detection medium since the electron transporting substance in the reagent part includes a water-soluble aromatic heterocycle compound (hereinafter, may also be simply referred to as an "aromatic heterocycle compound"). Since the aromatic heterocycle compound may simply function as a field for transporting electrons and it is not necessary that the aromatic heterocycle compound in itself is subjected to oxidation-reduction as in the case of a metal complex, the aromatic heterocycle compound is considered to have no dependency on a reaction potential in a system and to be a stable compound. As a result, the analysis device according to the present invention including the reagent part containing such a water-soluble aromatic heterocycle compound can have higher sensitivity and reliability than those conventionally used in the art, for example, when being applied to a sensor and/or the like.

In addition, by using such an analysis device, an analyte can be analyzed with better sensitivity and higher reliability than those conventionally used in the art.

More specifically, it is supposed that, when the water-soluble aromatic heterocycle compound is present in the reagent part, the molecules of the aromatic heterocycle compound are close to each other, the electron cloud of pi-electrons present to be perpendicular to the surfaces of the molecules of the aromatic heterocycle compound becomes an electron-transporting path, and, therefore, electrons are efficiently transported. In addition, it is supposed that the reason for not involving any oxidation-reduction reaction of the water-soluble aromatic heterocyclic compounds in itself is that the electron cloud of delocalized pi-electrons is utilized as the electron-transporting path.

Figure 1:
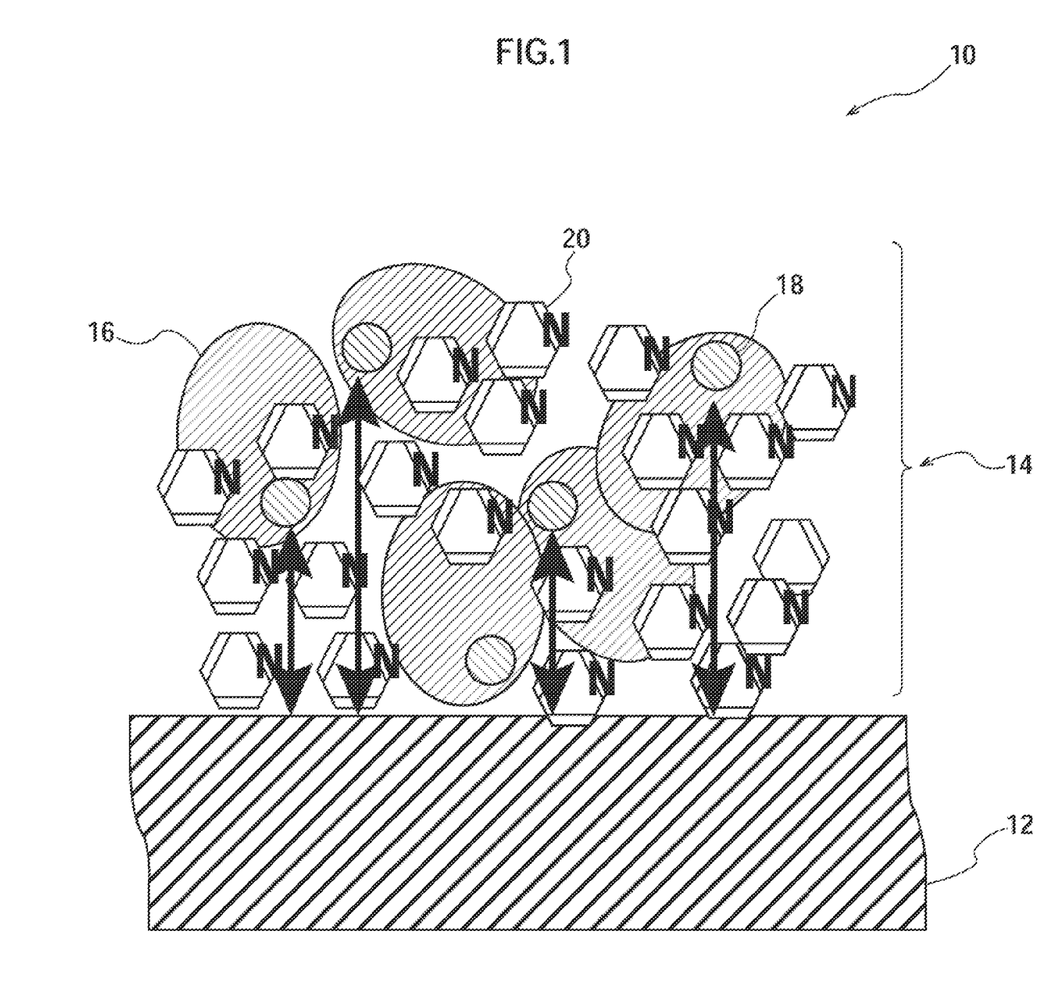
FIG. 1 is a conception diagram of an analysis device according to an exemplary embodiment of the present invention.

An analysis device according to an exemplary embodiment of the present invention is described taking as an example the case of using as an enzyme electrode, with reference to FIG. 1. However, the present invention is not bound by the following theory.

An electron transfer layer 14 as the reagent part is disposed on an electrode 12 as the electron detection medium in the enzyme electrode 10 and molecules of electron transfer compound(s) such as a oxidoreductase 16 are present to be independent of each other in the electron transfer layer 14. The active centers 18 of the molecules of the oxidoreductase 16 are not oriented in the same direction with respect to the electrode 12 because the active center 18 is often localized in a part of a molecule of the oxidoreductase 16. That is, in one molecule of the oxidoreductase, the active center 18 is placed in the vicinity of the electrode 12, and in another molecule of the oxidoreductase 16, the active center 18 is placed in a place away from the electrode 12. Therefore, the distances of electron transfer (directions of arrows in FIG. 1) between the active centers 18 of the oxidoreductase 16 and the electrode 12 are considered to be varied. When a distance from the active center 18 of a molecule of the oxidoreductase 16 to the electrode 12 is long, electron transfer between the oxidoreductase 16 and the electrode 12 by the oxidoreductase 16 alone becomes difficult.

According to the exemplary embodiment of the present invention, it is supposed that an aromatic heterocycle compound 20 (nitrogen-containing aromatic heterocycle compound in FIG. 1) is present between an oxidoreductase 16 and the electrode 12 in the electron transfer layer 14. Therefore, it is supposed that even when a distance between the active center 18 of an oxidoreductase 16 and the electrode 12 is long, if an aromatic heterocycle compound 20 is present therebetween, the aromatic heterocycle compound 20 enters into a gap between the oxidoreductase 16 and the electrode 12 and the aromatic heterocycle compound 20 and the oxidoreductase 16 overlap one another to construct an electron transfer pathway with the pi-electrons of the aromatic heterocycle compound 20.

Construction of such an electron transfer pathway allows electron transfer via the electron transfer pathway with an aromatic heterocycle compound 20 not only between an oxidoreductase 16 present at a position near to the electrode 12 and the electrode 12 but also between an oxidoreductase 16 present at a position farther away from the electrode 12 and the electrode 12.

As a result, electrons depending on the amount of an analyte which is present are transferred between the oxidoreductase 16 and the electrode 12 and are converted into the amount of the analyte in a sample by a detection system which is not illustrated, so that the presence or absence and amount of the analyte can be detected.

In the analysis device, the concentration of the electron transporting substance in the reagent part may be a concentration that allows transportation of electrons between the electron transfer compound and the electron detection medium and, for example, the concentration of the electron transporting substance may be from 10 mass % to 60 mass %, preferably from 10 mass % to 50 mass %, based on the total mass of the reagent part, when the electron transfer compound is present. When the concentration of the electron transporting substance is such a concentration, the molecules of the aromatic heterocycle compound included in the electron transporting substance around the analyte can become close to each other to construct the electron transfer pathway with a thickness enabling better electron transport. As a result, the analysis device with better sensitivity can be made.

In the analysis device, the aromatic heterocycle compound may be, for example, a nitrogen-containing aromatic heterocycle compound and, for example, is preferably at least one selected from the group consisting of pyridine, imidazole, and derivatives thereof. The analysis device with higher sensitivity can be made with, as the aromatic heterocycle compound, the nitrogen-containing aromatic heterocycle compound, for example, at least one selected from the group consisting of pyridine, imidazole, and derivatives thereof.

In the analysis device, the reagent part preferably includes an electron transfer compound which transfers electrons to or from an analyte and the electron transfer compound is, for example, an oxidoreductase. A naturally-occurring substance or a substance derived from a living body can easily be detected with higher sensitivity by incorporating the electron transfer compound such as an oxidoreductase into the reagent part. In the analysis device, the analyte may be, for example, a saccharide, and in this case, a saccharide can be detected with good sensitivity.

The term "step" as used herein encompasses not only an individual step but also a step in which an expected effect of this step is attained even when the step cannot be clearly distinguished from other step(s).

A numerical value range indicated by using "from A to B" as used herein refers to a range including A and B as the minimum and maximum values, respectively.

In the present invention, when a plurality of substances corresponding to one component are present in a composition, the amount of the component in the composition means the total amount of the plurality of substances present in the composition unless otherwise specified.

The present invention is described below.

The analysis device according to an exemplary embodiment of the present invention includes: an electron detection medium for obtaining information needed for analyzing an analyte in correlation with an electron transfer level; and a reagent part which is disposed on the electron detection medium and includes an electron transporting substance for transporting electrons between the analyte and the electron detection medium, wherein the electron transporting substance includes a water-soluble aromatic heterocycle compound, with the proviso that the electron transporting substance is free of a metal complex.

The electron detection medium is for obtaining information needed for analyzing an analyte in correlation with an electron transfer level, and preferably includes a conductive layer which can transfer electrons to or from the analyte and a supporting member for defining or ensuring physical characteristics of the electron detection medium, for example, defining a shape or ensuring rigidity, which are disposed in this order.

The reagent part is disposed on the electron detection medium and includes the electron transporting substance for transporting electrons between the analyte and the electron detection medium. In the reagent part, the electron transporting substance may be included in a layer placed on the electron detection medium. A layer that corresponds to the reagent part and includes the electron transporting substance is referred to herein as "electron transfer layer."

Electron Detection Medium (1) Supporting Member

The material of the supporting member may be either a material having insulating properties or a material having conductivity. As the supporting member having insulating properties, a commercially available engineering plastic such as polyethylene terephthalate, polyimide, polystyrene, or Duracon (registered trademark from Polyplastics Co., Ltd.) may be used.

As the supporting member having conductivity, for example, conductive carbon paper, a carbon fiber web, or a metal in plate, bar, or thin film form (e.g., gold or platinum) may be used. When the supporting member having conductivity is used, the supporting member may also function as a lead for taking an output from the analysis device.

The supporting member may be a member having sufficient rigidity in measurement. The supporting member may optionally have flexibility. The form of the supporting member is not particularly limited. The supporting member may have, for example, the form of a film or a rod, the form may variously be changed depending on a purpose.

The thickness of the supporting member may generally be from 0.1 mm to 1 mm, depending on the application of the analysis device, but is not limited thereto.

(2) Conductive Layer

The conductive layer in the electron detection medium is placed on the supporting member and includes a conductive substance which can transfer electrons to or from the electron transfer layer described below. By containing such a conductive substance, there are such advantages that, for example, the electron detection medium becomes an electric conductor and electrons can easily be detected as electric signals.

As the conductive substance, which is not particularly limited, a known substance which can transfer electrons may be used. Examples of such substances may include carbon materials, metals, metal-supported carbon, and the like, and one substance may be used singly or two or more substances may be used in combination.

A carbon material used as the conductive material may be used in the form of carbon particles or a structure in which carbon particles are high-density arranged or integrated. Examples of such carbon particles may include activated carbon, graphite, carbon black, and particles forming a higher-order structure, represented by diamond-like carbon, a carbon nanotube, or fullerene. Such structures in which carbon particles are high-density arranged or integrated include glassy carbon, pyrolytic graphite carbon, plastic-formed carbon, and/or the like. For example, such an advantage that molding to a desirable shape is enabled can be obtained by using such a carbon material. The carbon particles, which have primary particle sizes, for example, ranging from 3 nm to 150 nm, more preferably from 3 nm to 50 nm, are used. The conductive substance in which the carbon particles have such particle diameters has such an advantage that the specific surface area of the electron detection medium is increased or three-dimensional interaction of a fine structure may easily occur in electron transfer.

The metal as the conductive material may be present as metal particles in the conductive layer. When the metal particles are used, the metal particles may be present independently of the carbon particles or supported on the carbon particles.

Typical examples of such metal may include noble metals such as platinum (Pt), rhodium (Rh), gold (Au), silver (Ag), palladium (Pd), ruthenium (Ru), iridium (Ir), or osmium (Os), and one of these noble metals may be used alone or two or more thereof may be used in combination. Preferably, platinum is used alone or platinum and any one or more other noble metal(s) are used in combination.

When the metal is supported as the metal particles on the carbon particles, the particle size of the metal such a size that allows the metal particles to be suitably supported on the carbon particles, for example, a size of a colloid level ranging from 1 nm to 20 μm, preferably from 1 nm to 4 nm. The amount of the metal particles supported on the carbon particles may be, for example, from 0.1 part by mass to 60 parts by mass based on 100 parts by mass of the carbon particles. The amount of the metal particles supported on the carbon particles of not less than 0.1 part by mass can further improve sensitivity while the amount of not more than 60 parts by mass of the metal particles may provide, for example, a better relationship between the amount of the metal used and the sensitivity, and thus provide an economical advantage. Preferably, the amount of the metal particles supported on the carbon particles is from 0.5 part by mass to 40 parts by mass based on 100 parts by mass of the carbon particles.

The metal contained in the conductive layer may be present as a component in a different layer from that of the carbon particles. The conductive layer in this case may be composed of the layer having the carbon particles (carbon-containing layer) and the layer having the metallic element (metal-containing layer). As the kinds of metals which may be contained in the metal-containing layer, the above-mentioned metals may be applied as is. Such a metal-containing layer is preferably placed between the supporting member and the carbon-containing layer.

The forms of the above-mentioned carbon material and metal are not particularly limited and may be the forms of particles and any of other forms such as plate, rod, and thin film forms. The forms of the carbon and the metal may be identical to each other or different.

The thickness of the conductive layer may generally be from 0.01 μm to 10 μm but is not limited thereto, although varying according to the application of the analysis device.

Electron Transfer Layer

The electron transfer layer includes the electron transporting substance and preferably further includes an electron transfer compound which transfers electrons to or from an analyte.

The electron transfer layer may preferably be placed at a position allowing electron transfer to or from the electron detection medium. The electron transfer layer may be disposed in contact with the electron detection medium, but is not necessarily in contact with the electron detection medium, and, for example, another layer which does not interfere with electron transporting may be disposed between the electron transfer layer and the electron detection medium.

The thickness of the electron transfer layer may generally be from 0.1 μm to 5 μm but is not limited thereto, although varying according to the application of the analysis device.

(1) Electron Transfer Compound

The electron transfer compound in the analysis device may be a compound which transfers electrons, depending on the amount of an analyte which is present, to or from the analyte. Examples of such electron transfer compounds may include a compound involved in an enzyme reaction with an analyte. These electron transfer compounds may appropriately be selected depending on the application of the analysis device.

The electron transfer compound is preferably an enzyme, further preferably an oxidoreductase. In the analysis device using the enzyme as the electron transfer compound, electrons transferred between an analyte and the electron transfer compound can simply and easily be assessed as electrons depending on the amount of the analyte which is present, based on an enzyme-substrate relationship. Therefore, the analysis device is suitable for quantitatively measuring the concentration of a certain analyte in a sample, in which various substances are mixed, by a specific enzymatic reaction.

The oxidoreductase is an enzyme that catalyzes an oxidation-reduction reaction and a single enzyme or a combination of a plurality of different enzymes may be used in the same analysis device depending on the kind of an analyte and the details of detection of interest. Examples of the oxidoreductase include glucose oxidase (GOD), galactose oxidase, bilirubin oxidase, pyruvate oxidase, D- or L-amino acid oxidase, amine oxidase, cholesterol oxidase, choline oxidase, xanthine oxidase, sarcosine oxidase, L-lactate oxidase, ascorbate oxidase, cytochrome oxidase, alcohol dehydrogenase, glutamate dehydrogenase, cholesterol dehydrogenase, aldehyde dehydrogenase, glucose dehydrogenase (GDH), fructose dehydrogenase, sorbitol dehydrogenase, lactate dehydrogenase, malate dehydrogenase, glycerol dehydrogenase, 17B-hydroxysteroid dehydrogenase, estradiol 17B-dehydrogenase, amino acid dehydrogenase, glyceraldehyde 3-phosphate dehydrogenase, 3-hydroxysteroid dehydrogenase, diaphorase, cytochrome oxidoreductase, catalase, peroxidase, and glutathione reductase.

Especially, an oxidoreductase for a saccharide is preferable, and examples such oxideredutase include glucose oxidase (GOD), galactose oxidase, glucose dehydrogenase (GDH), fructose dehydrogenase, and sorbitol dehydrogenase.

The amount of the enzymes used is not particularly limited and may appropriately be set.

(2) Aromatic Heterocycle Compound as Electron Transporting Substance

The aromatic heterocycle compound included in the electron transfer layer is a water-soluble aromatic heterocycle compound. Incorporating the water-soluble aromatic heterocycle compounds in the electron transfer layer allows transportation of electrons between the electron transfer compound and the electron detection medium. An analysis device with favorable stability under aqueous environment, higher reliability and better sensitivity can be provided by incorporating such an aromatic heterocycle compound rather than a metal complex into the electron transfer layer. In addition, there is also such an advantage that the aromatic heterocycle compound does not depend on a reaction potential in a system.

In the present invention, the term "water-soluble" means dissolving in pure water of 20° C. in a mass ratio of 6% or higher under the environment at 20° C.

Since the water-soluble aromatic heterocycle compound includes an aromatic heterocycle, the electron clouds of pi-electrons can be formed to transport electrons. The aromatic heterocycle may be a five- or six-membered ring. The aromatic heterocycle may be a condensed or non-condensed aromatic heterocycle. Examples of the hetero atom include a nitrogen atom, an oxygen atom, and a sulfur atom.

The aromatic heterocycle compound may have at least one substituent on the aromatic heterocycle as long as the water-solubility of the compound is not impaired.

Examples of the substituent on the aromatic heterocycle of the aromatic heterocycle compound may include halogen atoms, amino group, alkyl groups, alkenyl groups, and alkoxy groups.

These substituents may further have at least one substituent, examples of which include ones mentioned as the examples of the substituents on the aromatic heterocycle.

The aromatic heterocycle compound may be, from the viewpoint of, for example, sensitivity, preferably a nitrogen-containing aromatic heterocycle compound, and examples of the nitrogen-containing aromatic heterocycle compound may include imidazole, pyrazole, pyridine, pyrimidine, purine, and derivatives thereof. The aromatic heterocycle compound is preferably, from the viewpoint of, for example, sensitivity, pyridine, imidazole or a derivative thereof, and is more preferably pyridine or a derivative thereof. Examples of pyridine or a derivative thereof may include pyridine and aminomethyl pyridine. One of such aromatic heterocycle compounds may be used singly, or two or more thereof may be used in combination. As the aromatic heterocycle compound, especially, aminomethyl pyridine is further preferred from a viewpoint of, for example, the sensitivity of the analysis device.

The aromatic heterocycle compound is preferably an aromatic heterocycle compound having a molecular weight of 1,000 or less, more preferably an aromatic heterocycle compound having a molecular weight of 800 or less. Therefore, in an embodiment, it is preferable that the aromatic heterocycle compound according to the present invention does not encompass an aromatic heterocycle compound having a molecular weight of more than 1,000, such as a polymer. When the aromatic heterocycle compound having a molecular weight of 1,000 or less is used, better transportation of electrons between the electron transfer compound and the electron detection medium may be attained.

The electron transfer layer may be a layer including the aromatic heterocycle compound(s) in a concentration that allows transportation of electrons between the electron transfer compound and the electron detection medium. As used herein, "concentration that allows transportation of electrons between an electron transfer compound and an electron detection medium" means a concentration at which at least between the electron transfer compound and the electron detection medium in the electron transfer layer the electron cloud of pi-electrons is present to be delocalized. Thus, when only a part of the electron transfer layer is in contact with the electron detection medium in the analysis device, the concentration of the aromatic heterocycle compound(s) may be a concentration that allows the transportation of electrons between the electron transfer compound and the electron detection medium in the region of the electron transfer layer in contact with the electron detection medium, and is not necessarily a concentration in the whole electron transfer layer.

The concentration that allows transportation of electrons between the electron transfer compound and the electron detection medium can specifically be varied according to the kind or concentration of the electron transfer compound used and, in an embodiment, the concentration of the aromatic heterocycle compound(s) may be 10 mass % or more, from 10 mass % to 60 mass %, preferably from 15 mass % to 50 mass %, based on the total mass of the electron transfer layer (reagent part) (when the whole electron transfer layer is in contact with the electron detection medium). The concentration of the aromatic heterocycle compound(s) according to the present invention means mass % based on the total mass that is the mass of the electron transfer layer including the aromatic heterocycle compound(s) together with an electron transfer compound and another additive that has been developed on the electron detection medium and has been dried.

The aromatic heterocycle compound may be subjected to crosslinking treatment or contained in and coated with a polymer. By being subjected to such treatment, the aromatic heterocycle compound is crosslinked between the molecules thereof or the aromatic heterocycle compound is crosslinked with an electron transfer compound, and can be maintained in an electron transfer layer for a long term. An analysis device having the electron transfer layer (reagent part) which is such a crosslinked substance allows the aromatic heterocycle compound to remain around a conductive layer and an analyte, for example, even in continuous measurement for a long term, so that a relative position to the conductive layer or the analyte can be further favorably maintained, for example, such an advantage as to be able to maintain a stable output is obtained.

The crosslinking treatment may be a crosslinking treatment that is commonly used in crosslinking of, for example, protein. Examples of crosslinking agents used for such crosslinking treatment may include glutaraldehyde and carbodiimide compounds, and succinimide esters. One of these crosslinking agents may be used alone or two or more thereof may be used in combination.

The amount of such an added crosslinking agent is not particularly limited if being a commonly used amount and may appropriately be set in a sufficient range such as, for example, 10 times or more that of a material to be crosslinked.

An electron transporting substance in the electron transfer layer includes the aromatic heterocycle compound, the electron transporting substance is free of a metal complex. Example of such a metal complex which is not included in the electron transporting substance according to the present invention include metal complexes conventionally used as so-called electron transport mediators. Specific examples of such a metal complex include osmium complexes.

Other Layers

The analysis device according to the present invention may include another layer(s) at any position as far as electron transfer between the electron detection medium and the electron transfer layer is possible. Examples of such other layers may include a protective layer, a layer for restricting penetration of substances, and a functional layer for modifying the surface of the electron detection medium; and the analysis device may include one or two or more in combination thereof.

The protective layer is not particularly limited as long as being able to protect the surface of the electron transfer layer or the analysis device. Examples of the protective layer may include cellulose acetate polymer, polyurea, polyamide, polyester, polyethylene oxide, polyvinyl alcohol, and lipid bilayer membranes.

The thickness of the protective layer is not particularly limited and may be, for example, from 0.5 µm to 5 µm.

Examples of a membrane for restricting penetration of substances in the analysis device, which membranes are intended to adjust the detection concentration range of an analyte, may include polyurea, polyamide, polyester, polyethylene oxide, and polyvinyl alcohol.

The thickness of the membrane for restricting penetration of substances is not particularly limited and may be, for example, from 0.5 μm to 5 μm.

Examples of the functional layers for modifying the surface of the electron detection medium, which layers are intended to improve the reactivity of a conductive member, may include thiol compounds, silane coupling agents, and lipid bilayer membranes.

The thickness of the functional layer is not particularly limited and may be, for example, from 0.001 μm to 5 μm.

Analyte

An analyte to be detected by the analysis device is not particularly limited as long as being a substance which can transfer electrons, depending on the amount of an electron transfer compound which is present, to or from the electron transfer compound and may be appropriately set according to the kind of the electron transfer compound.

For example, when the analysis device is used in a clinical application, various substrates contained in a clinical sample may be analytes. Examples of such clinical sample may include blood, serum, plasma, interstitial fluid, urine, sweat, tears, and saliva. Typical examples of the substrate may include glucose, uric acid, and glycosylated proteins.

For example, when the analysis device is utilized in a non-clinical application such as monitoring of fermentation, control of an industrial process, or environmental monitoring (e.g., suppression of efflux of liquid and gas and contamination), a food test, or veterinary medicine, various substrates contained in a non-clinical sample such as fermentation liquid, effluent, waste fluid, food, or milk may be an analyte.

Method for Producing Analysis Device

As a method for producing an analysis device, which is not particularly limited, any method in which each layer or each member as described above can be placed may be applied.

For example, by molding, shaping, or printing a mixture of components for a conductive layer, the conductive layer may be disposed on a supporting member to form an electrode, followed by disposing a layer of a liquid reaction mixture for an electron transfer layer containing an enzyme and an aromatic heterocycle compound.

In a case where crosslinking treatment of an electron transfer compound and an aromatic heterocycle compound in an electron transfer layer is performed, the method of crosslinking may vary depending on the kinds of the crosslinking agent and the aromatic compound. In an embodiment, a crosslinking agent may be incorporated into a reaction mixture, and the crosslinking may be performed simultaneously with forming an electron transfer layer. Alternatively, the crosslinking agent may be incorporated into a treatment liquid which is different from the reaction mixture, and after an analysis device is obtained without crosslinking as described above, the treatment liquid containing the crosslinking agent is applied to the electron transfer layer by adding, spraying, or immersing the liquid to perform crosslinking treatment.

As a print medium, for example, a film- or plate-like print medium may be used. The analysis device may be used after being removed from the print medium or may be used while being supported on the print medium. In the latter case, the print medium may function as a supporting member. The print medium may include a recess which is formed in the printed part of the mixture. In this case, a mask may be omitted.

It will be appreciated that drying during the production is preferably performed at a lower temperature than a temperature at which substantial deactivation of an enzyme occurs.

The analysis device according to the present invention can basically be formed only in a simple step such as forming a mixture, molding, and drying. That is, it can be expected to reduce a production cost to such a degree that a high mass-production technology can be utilized and a disposable analysis device can be produced.

The analysis method according to the present invention includes obtaining information needed for analyzing an analyte based on the electron transfer level of the analyte using the analysis device (referred to as an information obtaining step). In the analysis method, information for analyzing the analyte can be obtained with good sensitivity and high reliability because the analysis device as described above is used.

In the information obtaining step in the analysis method, the information needed for performing analysis is obtained based on the electron transfer level of the analyte. As used herein, "information needed" includes, for example, the amount, kind, and oxidation-reduction state of the analyte, time-dependent change in the analyte, and the like.

The analysis device as described above as an exemplary embodiment includes the conductive layer in the electron detection medium but the electron detection medium in the analysis toll of the present invention is not limited thereto. For example, the electron detection medium may include a color former.

When the electron detection medium includes a color former, the electron detection medium preferably has a configuration in which the color former is retained in a porous material insoluble in a sample. Typical examples of such a porous material may include a gelled material of, for example, polyacrylamide or polyvinyl alcohol. Examples of a color former include MTT (3-(4,5-dimethyl-2-thiazolyl)-2,5-diphenyl-2H-tetrazolium bromide), INT (2-(4-iodophenyl)-3-(4-nitrophenyl)-5-phenyl-2H-tetrazolium chloride), WST-4 (2-(4-iodophenyl)-3-(2,4-dinitrophenyl)-5-(2,4-disulfophenyl)-2H-tetrazolium, monosodium salt), and 4AA (4-aminoantipyrine).

Application

The analysis device according to the present invention is applicable to various applications because of having such an advantage that electrons can efficiently be transported to an electron detection medium through an electron transporting substance. Examples of such applications may include uses in, for example, an enzyme electrode; a sensor by which, as a platform, measurement of a substance by a colorimetric reaction system utilizing a color former and/or the like is performed; or the reaction system of a bio-fuel cell.

EXAMPLES

The present invention is described in detail below with reference to Examples. However, the present invention is not limited thereto at all. Unless otherwise specified, "%" is based on a mass.

Example 1

(1) Production of Enzyme Electrode

For an enzyme electrode, Pt (Au) was sputtered on a polyimide (PI) film to obtain a substrate having a platinum layer. As an electrode material, a printing ink in which 40 wt % Ketjen black (manufactured by Lion Corporation) was mixed with 40 wt % polyester resin as a binder and 20 wt % isophorone as a solvent was used. The surface of the polyimide film was printed with the printing ink so that the printing ink had a thickness of 10 μm.

Then, an enzyme liquid containing 1,250 U/ml of a wild-type GDH solution (0.1M MES buffer solution), 1% adonitol as a stabilizer, and 1 wt % of 4-aminomethyl pyridine as a water-soluble aromatic heterocycle compound was prepared.

The prepared enzyme liquid was dropwise added to the surface of the electrode using a precise syringe, and thereafter, the resulting electrode was left to stand for 4 hours under the environment of 23° C. and a relative humidity of <8% to be dried, whereby an enzyme electrode was obtained.

As a comparative enzyme electrode, a comparative enzyme electrode was produced in substantially the same manner as described above except that 4-aminomethyl pyridine was not added.

(2) Measurement by Enzyme Electrode

Figure 2:
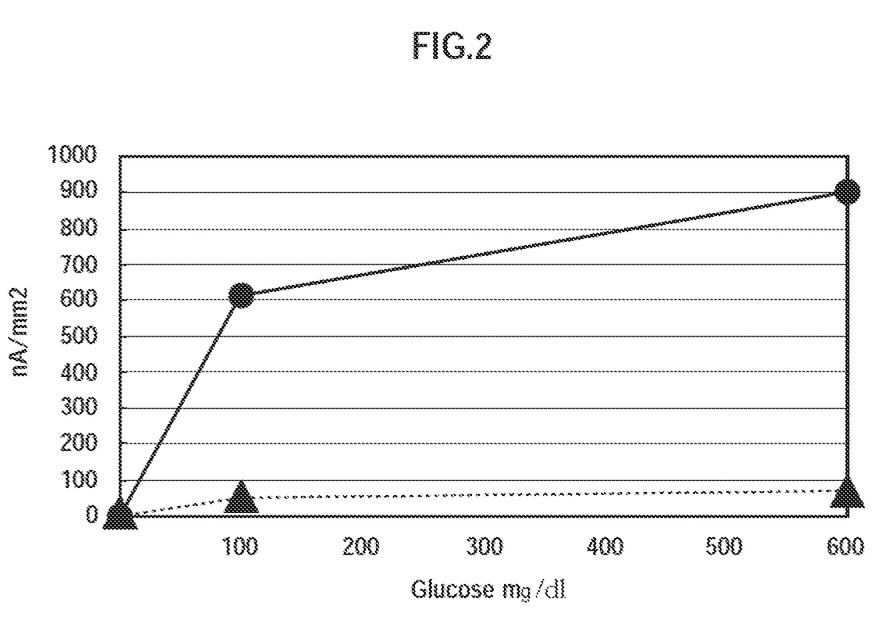
FIG. 2 is a graph indicating glucose response currents from enzyme electrodes in Example 1 of the present invention.

Electrode responses to glucose (100 mg/dL or 600 mg/dL) in 0.1 M phosphate buffer (pH 7.4) at 23° C. and +0.6 V (vs. Ag/AgCl) were detected by an amperometric method using the enzyme electrodes obtained as described above. The results are shown in FIG. 2. In FIG. 2, the black circles and the black triangles indicate measurements using the enzyme electrode added with 17% 4-aminomethyl pyridine and the comparative enzyme electrode added with no 4-aminomethyl pyridine, respectively.

As indicated in FIG. 2, about 13 times higher current density was detected in the glucose response current from the enzyme electrode containing 4-aminomethyl pyridine than that in the response current from the comparative enzyme electrode added with no 4-aminomethyl pyridine. This indicates that sensitivity is increased by using 4-aminomethyl pyridine as the aromatic heterocycle compound.

Example 2

(1) Production of Enzyme Electrode

For an enzyme electrode, Au was sputtered on a polyetherimide (PEI) film to obtain a substrate having a gold layer. As an electrode material, a printing ink in which 40 wt % Ketjen black (manufactured by Lion Corporation) was mixed with 40 wt % polyester resin as a binder and 20 wt % isophorone as a solvent was used. The surface of the polyetherimide film was printed with the printing ink so that the printing ink had a thickness of 10 μm, whereby a a working electrode was obtained.

Then, enzyme liquid containing 2,500 U/ml of a wild-type GDH solution (0.1 M MES buffer solution), 2% sucrose as a stabilizer, 1 v/v % glutaraldehyde as a crosslinking agent, and 1% of 4-aminomethyl pyridine as the aromatic heterocycle compound was prepared.

The prepared enzyme liquid was dropwise added to an electrode surface using a precise syringe and the resulting electrode was left to stand for 10 minutes at a normal temperature (23° C.) and a normal relative humidity (40% RH) to dry the surface. Then, the electrode was heat-treated at 40° C. for 15 minutes for drying, and then was left to stand for 2 hours under the environment of 23° C. and <2% RH for further drying, whereby an enzyme electrode was obtained.

As a comparative enzyme electrode, a comparative enzyme electrode was produced in substantially the same manner as described above except that 4-aminomethyl pyridine was not added.

(2) Measurement by Enzyme Electrode

Electrode responses to glucose in 0.1 M phosphate buffer (pH 7.4) were detected by voltammetry using the enzyme electrode obtained as described above. The voltammetry was performed at a sweep speed of 20 mV/s using the enzyme electrode produced in the above described (1), Pt, and Ag/AgCl as working, counter, and reference electrodes, respectively, at a measurement temperature of 37° C. A glucose concentration was 100 mg/dL or no glucose was added.

Figure 3:
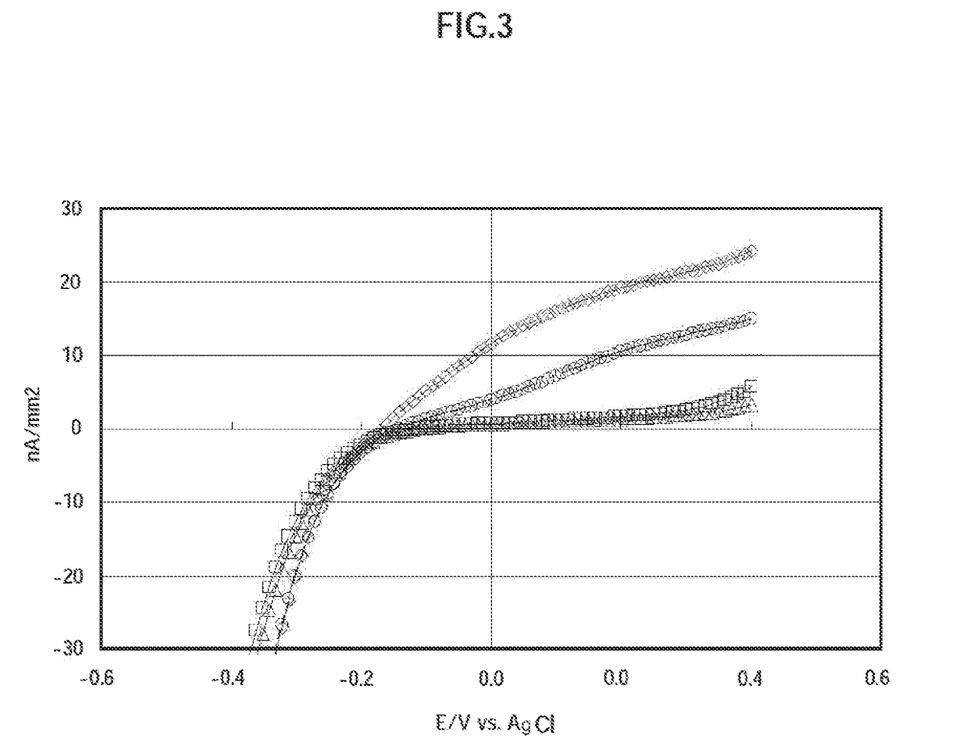
FIG. 3 is a voltammogram (oxidation wave) indicating glucose response currents from enzyme electrodes in Example 2 of the present invention.

The results are shown in FIG. 3 (third scan is indicated). In FIG. 3, the lozenges, the quadrangles, the circles, and the triangles indicate the measurement results in the case of 100 mg/dL glucose using the enzyme electrode added with 4-aminomethyl pyridine, the measurement results in the case of 0 mg/dL glucose using the enzyme electrode added with 4-aminomethyl pyridine, the measurement results in the case of 100 mg/dL glucose using the comparative enzyme electrode added with no 4-aminomethyl pyridine, and the measurement results in the case of 0 mg/dL glucose using the comparative enzyme electrode added with no 4-aminomethyl pyridine, respectively.

As indicated in FIG. 3, since a potential at which oxidization of glucose begins to occur is around −0.2 V with or without the addition of 4-aminomethyl pyridine and any specific peaks are not observed in the other potential regions, the oxidation-reduction of 4-aminomethyl pyridine in itself is not considered to occur.

Thus, it was exhibited that, in the enzyme electrodes added with 4-aminomethyl pyridine, oxidation-reduction of a compound in itself did not occur to transport electrons as in the case of a metal complex, and glucose was able to be stably detected with good sensitivity in the absence of an electron transfer mediator such as a metal complex.

Example 3

Enzyme electrodes 3A to 3F were obtained in substantially the same manner as in Example 2 (1) except that the concentrations of 4-aminomethyl pyridine were in the range of from 1% to 6% in preparation of enzyme solutions. In the final form of the enzyme electrodes, the concentrations of from 1% to 6% correspond to dry masses of from 23% to 64%, respectively.

Measurement for 100 mg/dL glucose in 0.1 M phosphate buffer (pH 7.4) was performed using the enzyme electrodes 3A to 3F and the comparative enzyme electrode containing no 4-aminomethyl pyridine produced in Example 2 (1), at a measurement temperature of 37° C. The enzyme electrodes 3A to 3F and the comparative enzyme electrode; Pt; and Ag/AgCl were used as working, counter, and reference electrodes, respectively. The results are shown in FIG. 4.

Figure 4:
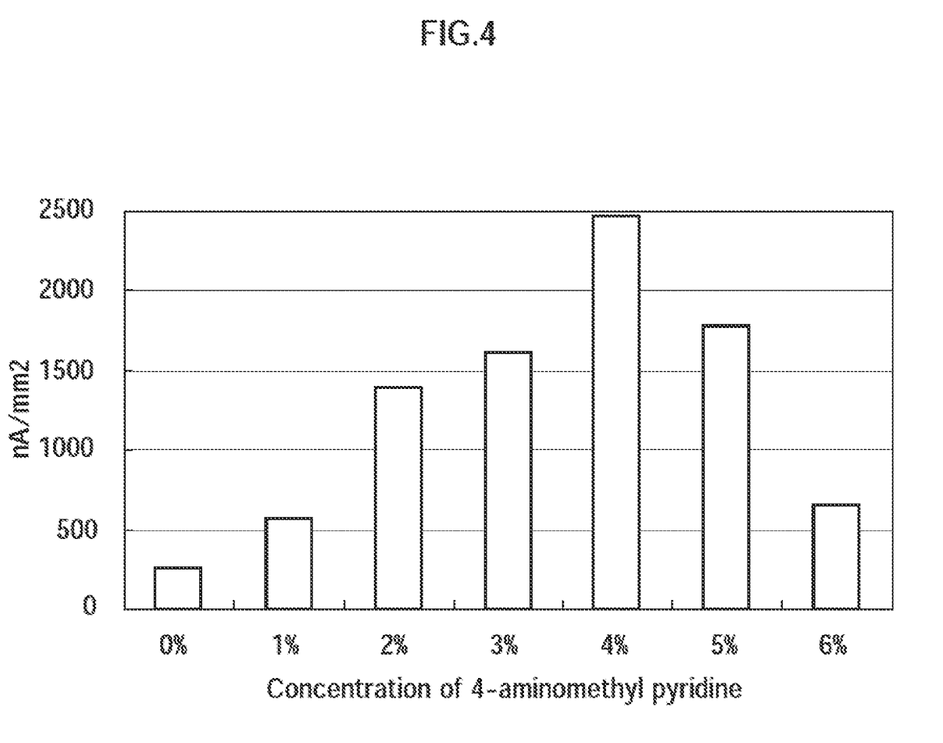
FIG. 4 is a graph indicating glucose response currents from enzyme electrodes in Example 3 of the present invention.

As indicated in FIG. 4, it is found that glucose can be detected by setting the concentrations of 4-aminomethyl pyridine added in the enzyme solutions to the range of from 1% to 6% (from 23% to 64% on a dry mass basis in final form). It is also found that respective sensitivities are improved by setting the concentrations of 4-aminomethyl pyridine into the range of from 2% to 5% (from 38 to 60% on a dry mass basis in final form), especially to 4% (55% on a dry mass basis in final form).

Example 4

Crosslinked enzyme electrodes 4A and 4B were obtained in substantially the same manner as in Example 2 (1) except that after dropwise adding of the prepared enzyme liquid to the electrode surface using a precise syringe and drying, glutaraldehyde was added to perform crosslinking treatment.

The crosslinking treatment was performed as described below. A dried electrode surface was gently rinsed with dH$_2$O and the electrode was immersed in 1 v/v % glutaraldehyde (GA) solution (containing 1% adonitol). After the immersion for 45 minutes or 120 minutes, each electrode was taken out and incubation was performed overnight in the environment of a room temperature and a low humidity (23° C. and <2%

RH). As a result, each of the enzyme electrodes 4A (treatment time of 45 minutes) and 4B (treatment time of 120 minutes) was obtained.

Figure 5:
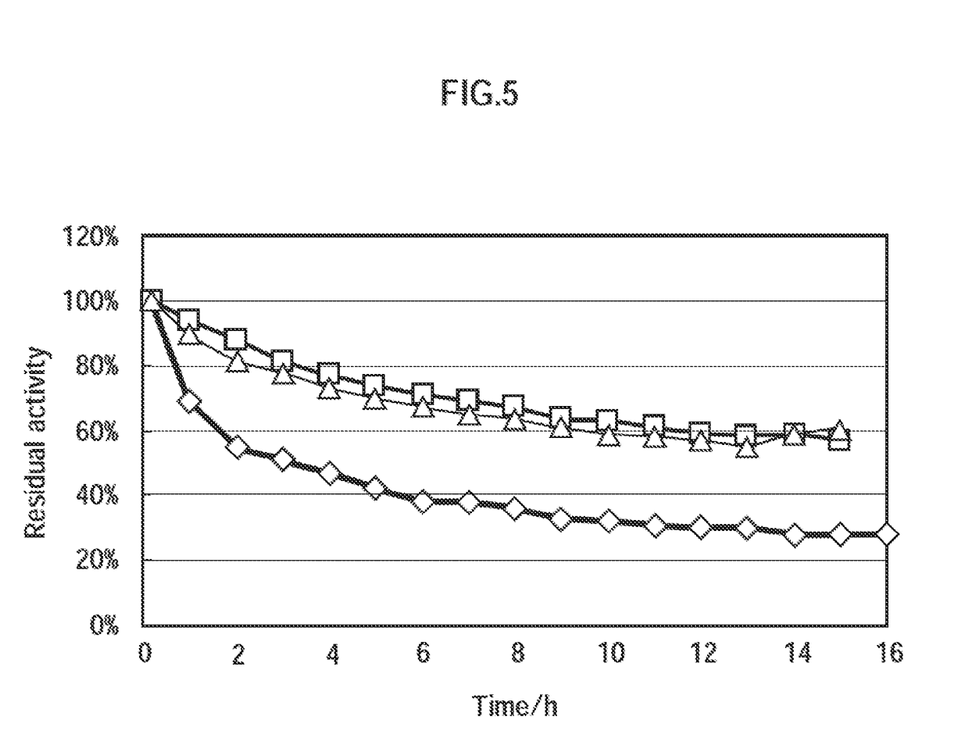
FIG. 5 is a graph in which stability is confirmed in continuous measurement of enzyme electrodes in Example 4 of the present invention.

Continuous measurement for glucose at a predetermined concentration was performed using each of the obtained enzyme electrodes 4A and 4B. For the continuous measurement, electrode responses to glucose in a phosphate buffer were detected by an amperometric method at 25° C. and +0.6 V (vs. Ag/AgCl) for 100 mg/dL glucose. The evaluation for a change in relative value over time, based on a current density just after the start of the measurement as an initial value of 100%, was performed. The results are shown in FIG. 5. In FIG. 5, the quadrangles, the triangles, and the lozenges indicate the cases of using the enzyme electrode 4A, the enzyme electrode 4B, and an uncrosslinked enzyme electrode, respectively.

As indicated in FIG. 5, it is found that, by performing the crosslinking treatment of 4-aminomethyl pyridine with glutaraldehyde, the localization of 4-aminomethyl pyridine is suppressed, the efflux from the electron transfer layer can also be prevented, and more stable outputs than that from the untreated enzyme electrode is maintained.

Example 5

Figure 6:
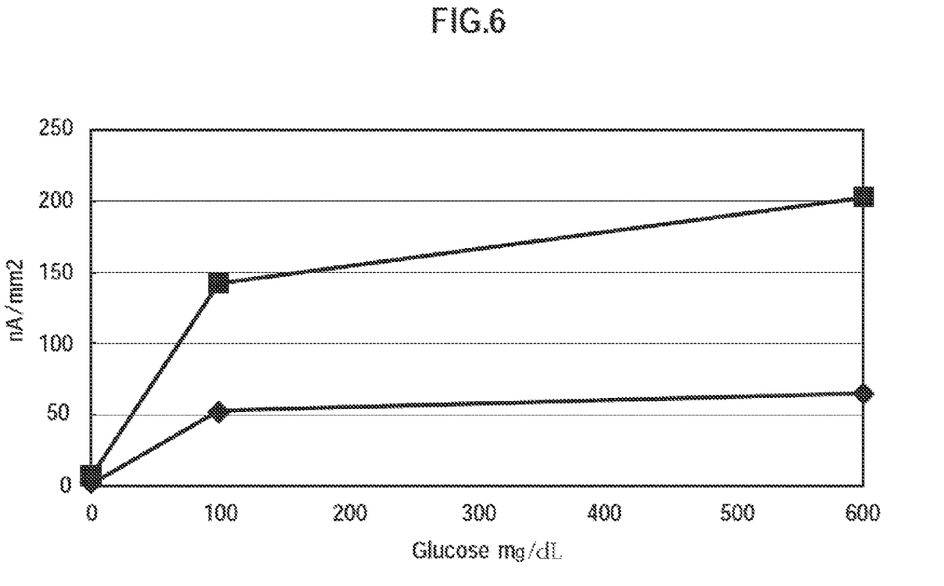
FIG. 6 is a graph indicating glucose response currents from enzyme electrodes in Example 5 of the present invention.

Electrode responses to glucose were detected in substantially the same manner as in Example 1 except that 5-amino-4-imidazolecarboxamide/HCl, instead of 4-aminomethyl pyridine, was added to be 17%. The results are shown in FIG. 6. In FIG. 6, the black quadrangles and the black lozenges indicate the cases of using the enzyme electrode added with 17% of 5-amino-4-imidazolecarboxamide and the comparative enzyme electrode added with no aromatic heterocycle compound, respectively.

As indicated in FIG. 6, it is found that the current densities are further favorably detected compared with the comparative enzyme electrode by using 5-amino-4-imidazolecarboxamide/HCl instead of 4-aminomethyl pyridine, as in the case of using 4-aminomethyl pyridine, and it was found that glucose can be detected with good sensitivity by using an imidazole derivative.

Comparative Example 1

Enzyme electrodes in Comparative Example were obtained in substantially the same manner as in Example 4 except that from 0.01% to 1.0% of poly(2-vinylpyridine) (weight molecular weight of about 21,000, Fluka Corporation) was used instead of 4-aminomethyl pyridine. Responses to 100 mg/dL of glucose were compared with relative values for an enzyme electrode containing no water-soluble aromatic heterocycle compound in substantially the same manner as in Example 4 except that the comparative enzyme electrodes were used. The results are shown in FIG. 7.

Figure 7:
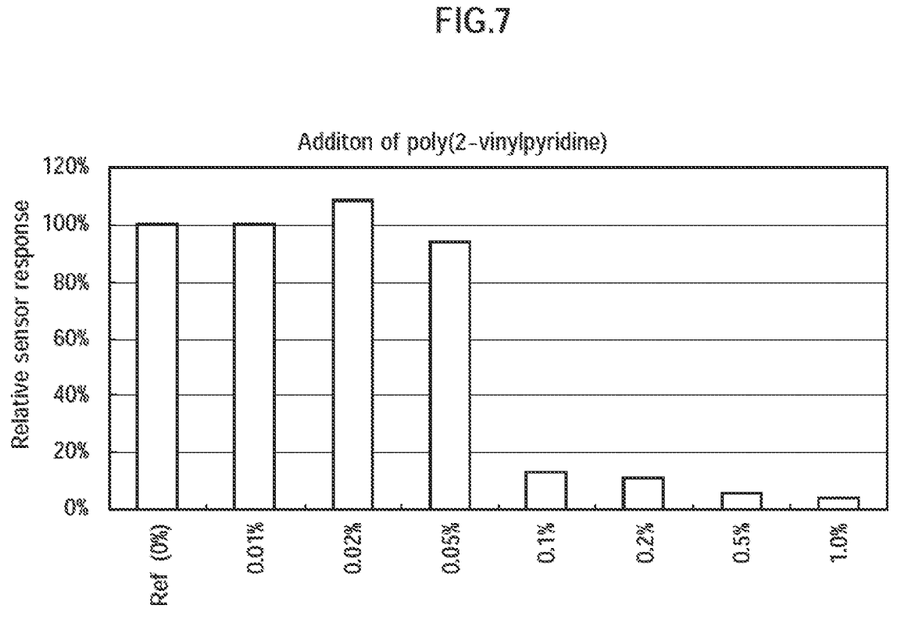
FIG. 7 is a graph indicating glucose response currents from enzyme electrodes in Comparative Example 1 of the present invention.

As indicated in FIG. 7, it was found that the responsiveness in the case of using poly(2-vinylpyridine) was similar to that in the enzyme electrode containing no water-soluble aromatic heterocycle compound or, at a concentration of 0.1% or more, was lower than that in the case of using the enzyme electrode containing no water-soluble aromatic heterocycle compound.

As described above, it is found that glucose in a sample can be detected with high sensitivity without treatment of adjusting the orientation of enzymes and without using any metal complex and/or the like, by using the enzyme electrodes of the present examples containing 4-aminomethyl pyridine. In addition, it is found that stable measurement is possible since 4-aminomethyl pyridine in itself is not involved in oxidation-reduction. Furthermore, the enzyme electrodes are hard to be affected by a reaction potential, unlike a metal complex and/or the like, and are applicable to a wide application such as a sensing device in a clinical situation represented by SMBG (self-monitoring of blood glucose), continuous blood glucose monitoring (CGM), or the like, a reaction system such as a bio-fuel cell, or a sensing device for industrial or environmental use in a non-clinical situation.

All references, patent applications, and technical standards described in the present specification are herein incorporated in their entirety by reference into the specification, to the same extent as if each individual reference, patent application or technical standard was specifically and individually indicated to be incorporated herein by reference.

What is claimed is:

1. An analysis device comprising:
    an electron detection medium to obtain information needed for analyzing an analyte in correlation with an electron transfer level; and
    a reagent part which is disposed on the electron detection medium and comprises an oxidoreductase that transfers an electron to or from the analyte, and
    electron transporting substances to transport electrons between the oxidoreductase and the electron detection medium,
    wherein the electron transporting substances comprise 4-aminomethyl pyridine or 5-amino-4-imidazolecarboxamide, and are free of a metal complex.

2. The analysis device according to claim 1, wherein a concentration of the electron transporting substances is from 10 mass % to 60 mass % based on a total mass of the reagent part.

3. The analysis device according to claim 1, wherein the reagent part further comprises a crosslinked substance obtained by crosslinking using at least one member selected from the group consisting of glutaraldehyde, carbodiimide compounds and succinimide esters.

4. The analysis device according to claim 1, wherein the electron detection medium is an electric conductor.

5. The analysis device according to claim 1, wherein the analyte is a saccharide.

6. The analysis device according to claim 1, wherein the electron transporting substances comprise 4-aminomethyl pyridine.

7. The analysis device according to claim 1, wherein the electron transporting substances comprise 5-amino-4-imidazolecarboxamide.

8. An analysis method comprising
    transporting electrons in a reagent part of an analysis device by electron transporting substances between an analyte and an electron detection medium, wherein
        the reagent part is disposed on the electron detection medium and comprises an oxidoreductase that transfers an electron to or from the analyte, and
        the electron transporting substances that transport electrons between the oxidoreductase and the electron detection medium comprise 4-aminomethyl pyridine or 5-amino-4-imidazolecarboxamide, and are free of a metal complex; and
    obtaining information about the analyte based on an electron transfer level of the analyte by the transporting electrons step.

9. The analysis method according to claim 8, wherein a concentration of the electron transporting substances is from 10 mass % to 60 mass % based on a total mass of the reagent part.

10. The analysis method according to claim 1, wherein the reagent part further comprises a crosslinked substance obtained by crosslinking using at least one selected from the group consisting of glutaraldehyde, carbodiimide compounds and succinimide.

11. The analysis method according to claim 8, wherein the electron detection medium is an electric conductor.

12. The analysis method according to claim 8, wherein the analyte is a saccharide.

13. The analysis method according to claim 8, wherein the electron transporting substances comprise an electron cloud of pi-electrons perpendicular to the surfaces of the molecules of 4-aminomethyl pyridine or 5-amino-4-imidazolecarboxamide.

14. The analysis method according to claim 8, wherein the information includes an amount, kind, or oxidation-reduction state of the analyte, or a time-dependent change in the analyte.

15. The analysis method according to claim 8, wherein the electron transporting substances are not a polymer.

* * * * *